United States Patent [19]
Steele et al.

[11] Patent Number: 5,312,411
[45] Date of Patent: May 17, 1994

[54] UNI-COMPARTMENTAL FEMORAL KNEE INSTRUMENTS AND PROSTHESIS

[75] Inventors: John K. Steele; Thomas A. Carls, both of Memphis; David L. Evans, Bartlett; Carol D. Taylor, Memphis, all of Tenn.; Philippe Cartier, Paris, France; James Andrews, Birmingham, Ala.; William Kennedy, Sarasota, Fla.

[73] Assignee: Smith & Nephew Richards, Inc., Memphis, Tenn.

[21] Appl. No.: 967,161

[22] Filed: Oct. 27, 1992

[51] Int. Cl.$^5$ ............................................... A61B 17/56
[52] U.S. Cl. ........................................ 606/88; 606/96; 606/79
[58] Field of Search ............... 606/80, 88, 96, 104; 144/2-9; 623/16, 20

[56] References Cited

U.S. PATENT DOCUMENTS

| | | | |
|---|---|---|---|
| 2,607,339 | 8/1952 | Price | 606/96 |
| 2,697,433 | 12/1954 | Zehnder | 606/96 |
| 4,119,092 | 10/1978 | Gil | 606/96 |
| 4,325,373 | 4/1982 | Slivenko et al. | 606/96 |
| 4,570,624 | 2/1986 | Wu | 606/96 |
| 4,721,104 | 1/1988 | Kaufman et al. | 606/88 |
| 4,777,942 | 10/1988 | Frey et al. | 606/80 |
| 4,865,025 | 9/1989 | Buzzi et al. | 606/96 |
| 5,053,039 | 10/1991 | Hofmann et al. | 606/86 |
| 5,098,436 | 3/1992 | Ferrante et al. | 606/88 |

FOREIGN PATENT DOCUMENTS 1161102  6/1985  U.S.S.R. .............................. 606/96

*Primary Examiner*—David Isabella
*Attorney, Agent, or Firm*—Pravel, Hewitt, Kimball & Krieger

[57] ABSTRACT

A surgical instrument for shaping the distal femur of a patient to receive a unicondylar prosthetic component includes a cutting guide body that carries a pair of cylindrically shaped openings in the guide body, each of the openings having a central longitudinal axis and the respective axes of the openings forming an acute angle. An annular bushing is removably received in a selected one of the cylindrical openings during a cutting of the distal femur. A bone cutting reamer registers with a central cylindrical opening in the bushing. The bone cutting reamer has an annular shoulder that abuts the top of the bushing to define the depth of cut. During use, the surgeon positions the cutting guide body over a diseased condyle of the patient's distal femur. The surgeon then sequentially places the bushing and its associated bone cutting reamer into one of the selected openings of the cutting guide body. After placing the bone cutting reamer in the second opening of the guide body, the surgeon has formed two overlapping circular cuts which form an elongated oval shaped and three-dimensionally convex surface for receiving the unicondylar prosthesis.

13 Claims, 5 Drawing Sheets

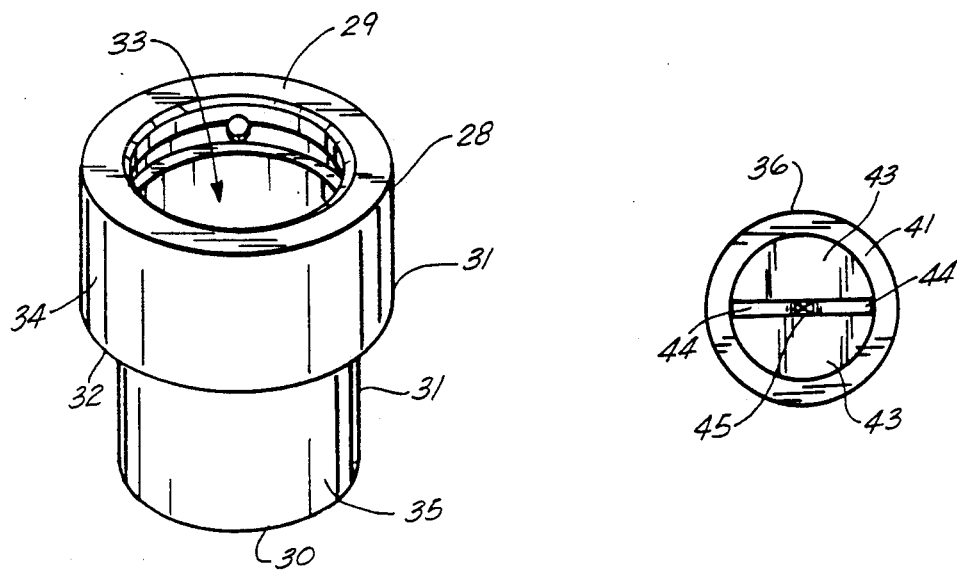
FIG. 3
FIG. 6
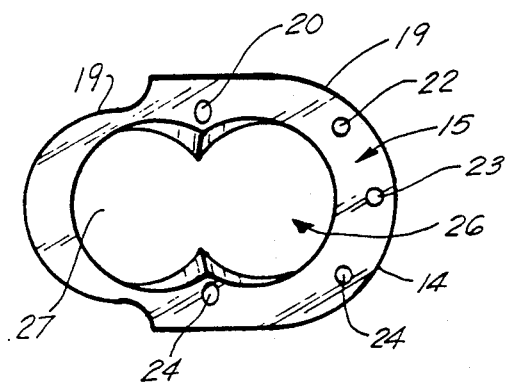
FIG. 4
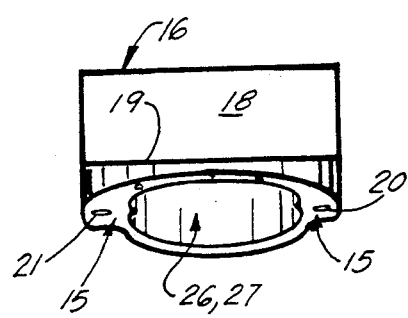
FIG. 5

1

UNI-COMPARTMENTAL FEMORAL KNEE INSTRUMENTS AND PROSTHESIS

BACKGROUND OF THE INVENTION

1. Field Of The Invention

The present invention relates to orthopedic surgical instruments and prosthetic devices and more particularly relates to an improved instrument for cutting the distal femur of a patient to receive a unicondylar prosthetic component and such a unicondylar prosthesis. Even more particularly, the present invention relates to improved surgical instrumentation for shaping the distal femur of a patient to receive a unicondylar prosthetic component wherein a cutting guide body has a pair of cylindrically shaped, overlapping openings which are angled with respect to each other and wherein a surgeon can make sequential dished cuts in the patient's distal femur by placing a rotary reamer in one of the angled openings and then in the other of the angled openings to produce an overlapping, oval shaped convex surface on the diseased condylar portion of the distal femur. The prosthesis has a distal surface which is shaped to fit the prepared bone surface.

2. General Background

Various types of instruments and methods have been developed to enable a surgeon to affix a distal femoral knee prosthesis to the human femur. The femoral prosthesis may be a bi-condylar prosthesis as used in total knee arthroplasty, or it may be a unicondylar prosthesis where only one condyle of the femur is affected and thus in need of replacement.

The purpose for affixing such a prosthesis is to restore the patient's ability to walk after disease or other traumatic causes affecting the knee which have impaired that ability. It is important that the prosthesis be attached to the femur in such a manner that it will approximate as closely as possible, the natural femoral condyle(s). Therefore, the initial shaping of the distal end of the femur is critically important.

A British patent No. 1,534,263 issued to Goodfellow utilizes a concave cutting tool to prepare the distal end of one condyle, the prosthesis having a rear surface which has a portion curved in three dimensions and another portion with an axis of rotation parallel to the axis of the femoral shaft.

U.S. Pat. No. 4,719,908 to Averill et al utilizes a contouring guide for guiding a burr assembly along a condyle for preparing the surface to receive an unicondylar prosthesis. A prosthetic implant is then implanted which has an inner surface that matches the curved contour formed as a result of the configuration of the guide.

Some methods and devices for cutting the distal femur use the central longitudinal axis of the femur (i.e. intramedullary canal) as an aid in shaping the distal femoral surface. These prior art methods and devices insert an alignment rod into the intramedullary canal of the femur. The alignment rod protrudes a substantial distance from the femur after it is inserted. Cutting guides and drill templates are then positioned on or around the rod in an abutting contact with the condyles of the femur in order that the surgeon can accurately resect the condyles and/or drill holes in them. Once the distal femur is properly shaped for receiving the femoral prosthesis, the physician may attach it to the distal femur.

U.S. Pat. No. 4,474,177 issued to Whiteside shows a device that uses the intramedullary canal of the femur for shaping and drilling the femoral condyles (see for examples FIGS. 8-23 of Whiteside). The Whiteside device could be used in a unicondylar replacement operation or in a total knee replacement.

Other patents have issued which describe methods for shaping a distal femoral surface.

The following listed patents describe devices for shaping the distal femoral condyles and without using an intramedullary stabilizing spike:

| U.S. Pat. No. | Assignee/Patentee |
| --- | --- |
| 4,926,847 | Johnson & Johnson |
| 4,892,093 | Osteonics Corp |
| 4,773,407 | T. D. Peterson |
| 4,721,104 | Dow Corning Wright |
| 4,718,413 | Orthomet Inc. |
| 4,574,794 | Queen's Univ. Kingston |
| 4,566,448 | W. L. Rohr |
| 4,524,766 | T. D. Peterson |
| 4,502,483 | Dow Corning Corp |
| 4,457,307 | W. T. Stillwell |
| 4,349,018 | G. R. Chambers |
| 327387 EPO | J. W. Goodfellow |

Other devices are used for shaping the femoral condyles which use an intramedullary spike:

| U.S. Pat. No. | Assignee/Patentee |
| --- | --- |
| 4,935,023 | Dow Corning Wright |
| 4,907,578 | T. D. Peterson |
| 4,825,857 | Howmedica |
| 4,759,350 | H. K. Dunn |
| 4,738,254 | Biomed Eng. Trust |
| 4,738,253 | Biomed Eng. Trust |
| 4,722,330 | Dow Corning Wright |
| 4,703,751 | K. P. Pohl |
| 4,653,488 | Howmedica |
| 4,646,729 | Howmedica |
| 4,567,885 | G. W. Androphy |
| 4,487,203 | G. W. Androphy |
| 4,474,177 | Wright Manf. Co. |

U.S. Pat. Nos. 4,787,383; 4,567,886; and 4,211,228 are patents directed to devices for shaping either the femur condyles or the tibial surface.

U.S. Pat. Nos. 4,959,066 and 4,621,630 illustrate devices for operating on the proximal end of the femur.

SUMMARY OF THE PRESENT INVENTION

The present invention provides improved instrumentation and a prosthetic implant for use in knee arthroplasty surgical procedures when only one condyle of the knee is to be affected. The instrument includes a reamer guide having two apertures adjacent and in communication with one another which can be affixed with bone spikes over the exposed distal end of a diseased femoral condyle.

A cylindrical bushing is received within one of the two apertures. A bone cutting reamer is then received within the bushing and extends to a predetermined depth as controlled by the abutting contact between the bushing and a stop collar portion of the reamer.

The cutting end of the reamer is arcuately shaped. The combination of the reamer and the reamer guide provide for the formation of arcuate reaming of the condylar surface to provide overlapping convex cuts so that an elongated oval shaped and three-dimensionally convex shape is formed on the diseased condylar surface.

After the reamer is used to cut bone tissue at one of the openings in the reamer guide, the bushing and reamer are then inserted into the other reamer guide opening and bone matter is again removed.

After the condyle is reamed from both apertures, the guide is removed and the condyle is left with the elongated oval shaped convex surface. Preparation of the condyle is completed by squaring off the posterior surface of the bone by cutting it using known techniques and forming a pin hole and slot to accommodate the implant. The implant has a typical, smoothly curved outer bearing surface which is designed to engage the bearing surface on the proximal end of the tibia or a prosthetic implant mounted on that end. The inner surface has three surfaces shaped and dimensioned to mate with the prepared distal end of the femur. Bone cement can be used as an interface between the implant and the bone tissue.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 3 is a partial perspective view of the preferred embodiment of the apparatus of the present invention illustrating the bushing portion thereof;

FIG. 4 is a bottom fragmentary view of the preferred embodiment of the apparatus of the present invention illustrating the cutting guide body;

FIG. 5 is a fragmentary end view of the cutting guide body portion of the preferred embodiment of the apparatus of the present invention;

FIG. 6 is a fragmentary end view of the preferred embodiment of the apparatus of the present invention illustrating the bone cutting reamer portion thereof;

DETAILED DESCRIPTION OF THE PREFERRED EMBODIMENT

Figure 1:
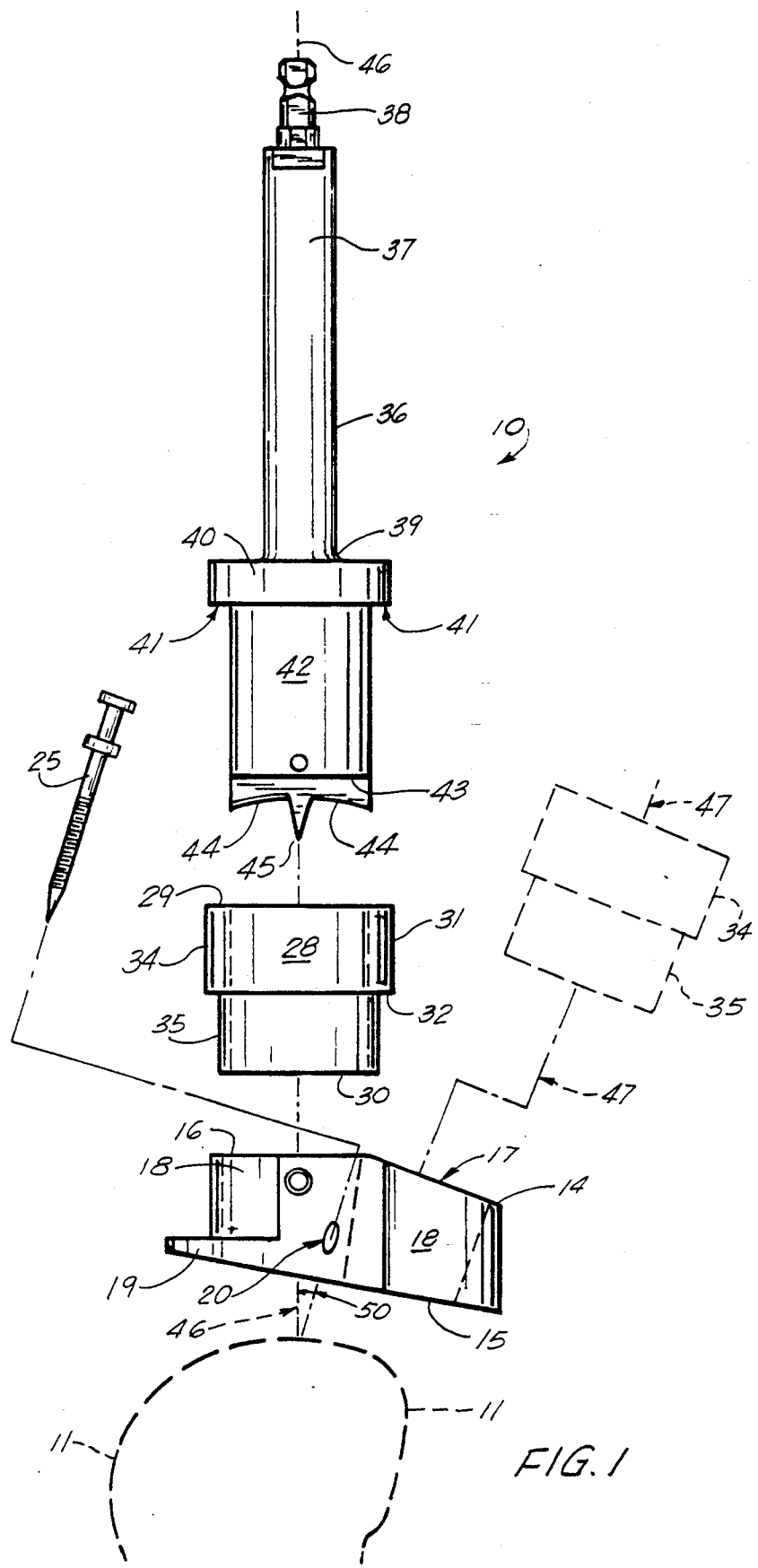
FIG. 1 is an exploded lateral view of the preferred embodiment of the apparatus of the present invention.
Figure 2:
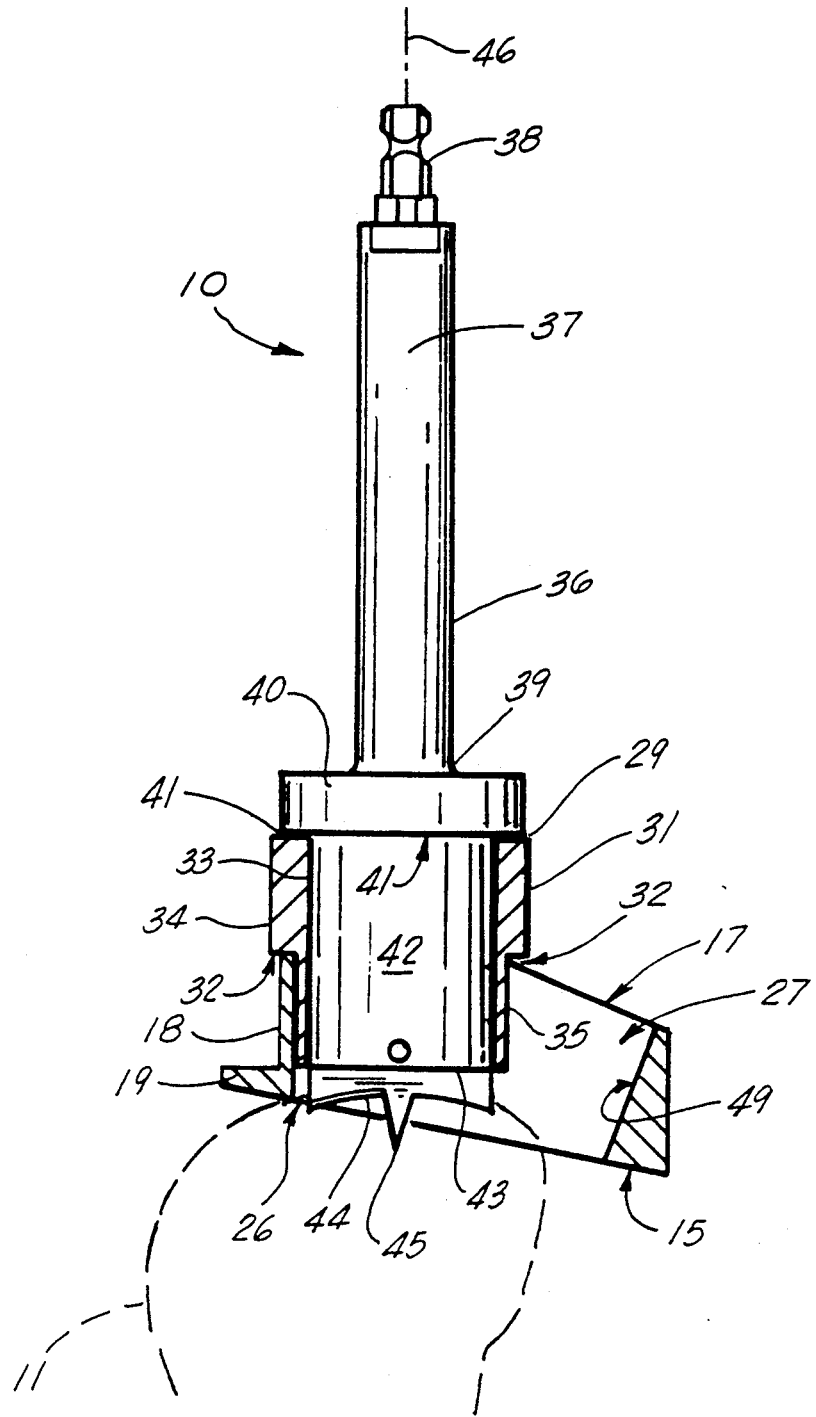
FIG. 2 is a lateral, sectional view of the preferred embodiment of the apparatus of the present invention shown in assembled, in-use position upon a patient's distal femur.

FIGS. 1 and 2 show generally the preferred embodiment of the apparatus of the present invention designated generally by the numeral 10. Femoral cutting instrumentation 10 includes a guide body that can be placed in a selected position by a surgeon upon a patient's distal femur. More particularly, guide body 14 is placed upon a diseased condyle 12 or 13 and is used to prepare the diseased condyle 12 or 13 for receiving a unicondylar prosthesis as part of the surgical procedure.

Guide body 14 is shown in FIGS. 1-2 and 3-4. Guide body 14 has a generally flat bottom 15, and an upper portion that includes a first upper surface 16 and a second upper surface 17. The upper surfaces 16, 17 are angled with respect to each other as shown in FIG. 1. Guide body 14 has a peripheral side wall 18 that defines a pair of cylindrically shaped openings 26, 27. Flange 19 carries a plurality of cylindrically shaped openings 22-24 which help affix guide body 14 over a particular diseased condyle as selected by the surgeon for preparation.

A pair of diagonal openings 20, 21 extend from side wall 18 downwardly to bottom surface 15 of guide body 14. The diagonal openings 20, 21 are shown in FIG. 3 as communicating with sidewall 18 and with the bottom surface 15. A bone spike 25 can be driven by the surgeon through each of the openings 20, 21 so that the bone spike 25 penetrates the distal femur 11. In this fashion, bone spike 25 placed through the openings 20, 21 can be used to fasten guide body 14 upon the distal femur 11 in a selected position. Openings 22-24 in flange 19 can also be used for the placement of bone spikes, screws or like fasteners for further securing guide body 14 to the distal femur 11 at a selected position upon a particular diseased condyle 12 or 13.

The pair of cylindrically shaped openings 26, 27 are defined by respective inside wall portions 48, 49 of guide body 14. Each cylindrically shaped opening 26, 27 of guide body 14 has a central longitudinal axis. The cylindrical opening 26 has a central longitudinal axis 46. The cylindrical opening 27 has a central longitudinal axis 47. An angle 50 defines the angle between axis 46 and axis 47.

Each generally cylindrically shaped opening 26, 27 overlaps the other as shown in FIGS. 1, 2, and 3. This combination of an overlapping of the cylindrically shaped openings 26, 27 in combination with the angled orientation of the axis 46, 47 of each respective opening 26, 27 is used to create overlapping cuts in the selected condyle 12 or 13 of the distal femur 11.

Cylindrical bushing 28 has an upper end 29, a lower end 30 and an annular side wall 31. The bushing 28 includes a larger diameter section 34 and a smaller diameter section 35 so that an annular shoulder 32 is provided between the larger section 34 and the smaller section 35. The outside diameter of smaller diameter section 35 is sized to register within and closely fit cylindrically shaped opening 26. Smaller diameter section 35 is sized as well to closely fit cylindrically shaped opening 27. In this fashion, the bushing 28 can be selectively placed in cylindrically shaped opening 26 or 27 so that bone cutting reamer 36 can make multiple cuts in the selected condyle 12 or 13 of the distal femur 11. Annular shoulder 32 defines a stop against upper surface 16 or upper surface 17 when the bushing 28 is placed respectively in either opening 26 or opening 27. Bushing 28 has a longitudinally extending bore 33 that receives bone cutting reamer 36 during use.

Bone cutting reamer 36 comprises an elongated shaft 37 having a hexagonal end portion 38 for attachment to a driving tool, drill, or the like. The lower end portion 39 of shaft 37 forms an integral connection with annular collar 40. Annular collar 40 has a lower surface in the form of annular shoulder 41 which engages the upper end 29 of bushing 28 during use.

Bone cutting reamer 36 further comprises a lower end portion 42 that is cylindrically shaped and having an external diameter that corresponds to the internal diameter of longitudinal bore 33 of bushing 28. During use, when bone cutting reamer 36 is assembled to bushing 28, the lower end portion 42 registers in bore 33 and annular shoulder 41 abuts against upper end 29 of bushing 28, thus functioning as a stop to limit the depth of cut of bone cutting reamer 36 into distal femur 11. In this fashion, the combination of bushing 28, the size of guide 15, and the size of bone cutting reamer 36 lower end portion 42 controls how much bone is cut in a particular surgical procedure.

Figure 7:
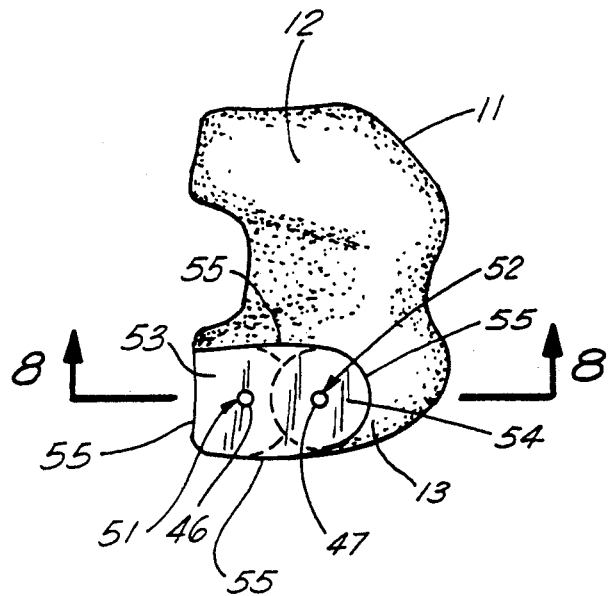
FIG. 7 is a schematic end view of a patient's distal femur after a cutting of one of the condyles using the femoral knee instrumentation of the present invention.
Figure 8:
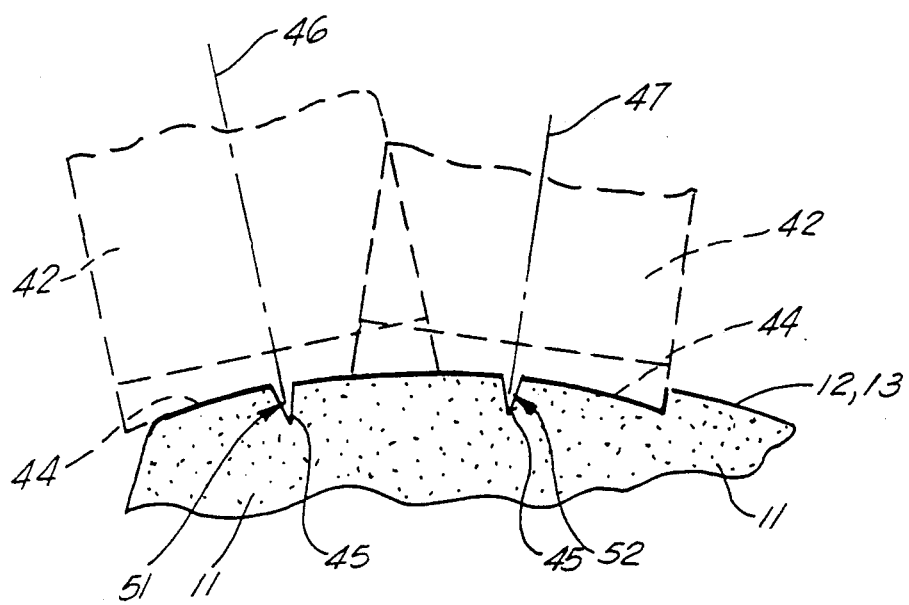
FIG. 8 is a sectional view taken along line 8—8 of FIG. 7.

Bone cutting reamer 36 provides a flat distal end 43 that carries an arcuate cutting blade 44. The middle portion of arcuate cutting blade 44 communicates with drill cutting tip 45. In FIG. 7, openings 51, 52 are openings formed by cutting tip 45 portion of bone cutting reamer 36. In FIG. 8, generally circular, convex surfaces 53, 54 are formed by blade 44 on the patient's distal femur 11 in overlapping fashion, the entire convex surface area being an oval shape and designated by the numeral 55.

Guide body 14 can be made of a suitable structure material such as stainless steel or the like. Likewise, bone cutting reamer can be of a surgical instrument metallic construction. The cylindrically shaped lower end portion 42 of bone cutting reamer 36 can be highly polished so that it can closely abut the vertical bore 33 of bushing 28 and generate minimum friction during use. Bushing 28 can be of a plastic construction for example. Set screws can be used to affix bushing 28 in a selected opening 26, 27 to prevent shifting or movement during the drilling operation.

Figure 11:
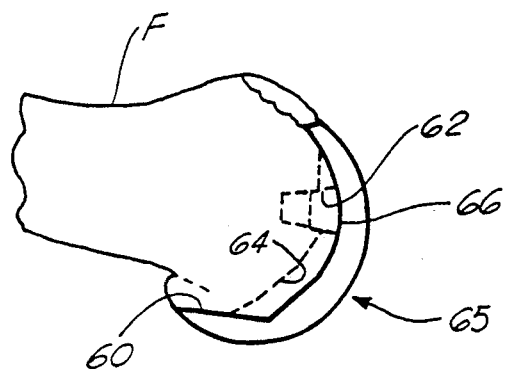
FIG. 11 is a side plan view showing the implant mounted on the distal end of a femur.

After the cuts shown in FIG. 8 are completed, the anterior portion of the distal end of the femur F is squared off by using known cutting techniques to provide a flat surface 60 as shown in FIG. 11. An opening 62 and a groove 64 are formed in the distal end of the prepared surface of the femur in order to accommodate a pin and rib formed on the implant 65, described below.

Figure 10:
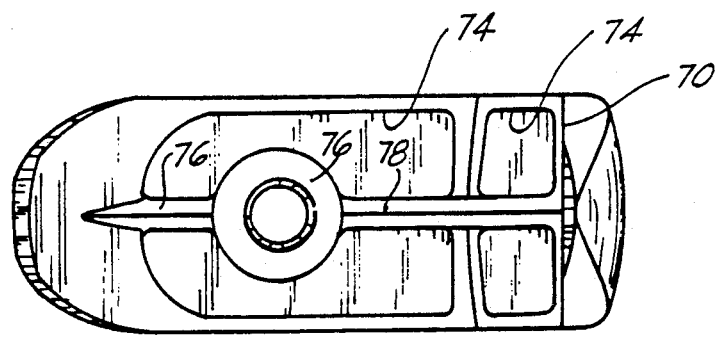
FIG. 10 is a top plan view of the implant of FIG. 9.
Figure 9:
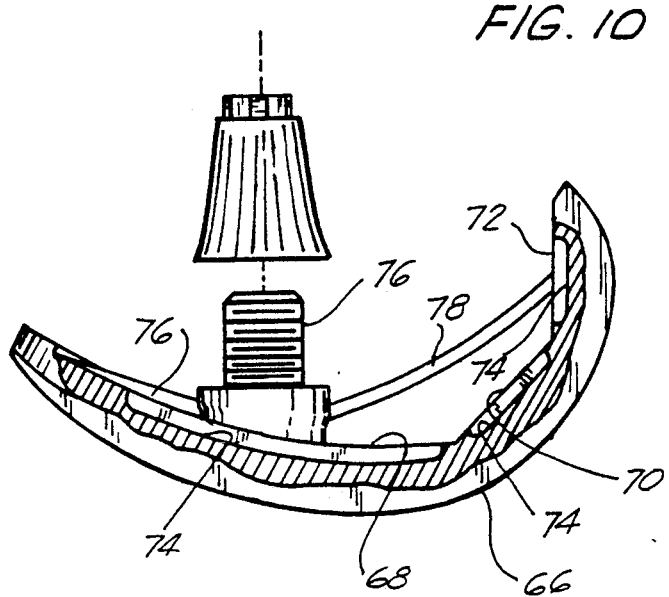
FIG. 9 is a side plan view, partially in section, of the inventive prosthetic implant.

The inventive unicondylar implant 65 is shown in FIGS. 9–11, where a typical, smoothly curved, outer bearing surface 66 is formed with an inner surface that has three basic surfaces for mating with the distal end of the femur. These surfaces include a first surface 68 which is generally in the shape of a spherical section, and a second flat surface 70 and a third flat surface 72 which are designed to mate with the squared off surface 60. Each of the surfaces has hollowed out portions 74 in order to accommodate bone cement which is used to help anchor the prosthesis to the distal end of the femur.

A threaded pin 76 is formed on the surface 68 for receiving a threaded fixation lug 77 which engages the opening 62 formed in the distal end of the femur. A pair of ribs 74, 78 extend along the center line of the inner surface of the prosthesis from the pin 76 to the surfaces 68 and 70, respectively, for adding stability and resistance to torsional movement for the implant.

The surfaces 68 and 70 are designed to mate with the surfaces formed through the use of the instruments described above so that a accurately fitting prosthesis as shown in FIG. 11 is provided.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A surgical instrument for shaping the distal femur of a patient to receive a unicondylar prosthetic component, comprising:
   a) a cutting guide body having a peripheral sidewall, a bottom surface for abutting the patient's distal femur during use, and a top surface for receiving a bone cutting reamer;
   b) means for affixing the guide body to the distal femur in a desired position;
   c) a pair of cylindrically shaped openings in the guide body surrounded by the peripheral side wall of the guide body, said openings extending between the upper and lower surfaces of the guide body;
   d) each of the openings providing a central axis, and the respective axes of the openings forming an acute angle;
   e) a bone cutting reamer that registers in a selected opening of the guide body, wherein the opening positions the reamer for shaping the distal femur of a patient; and
   f) wherein a portion of the openings is overlapping so that the cuts formed by the reamer when placed sequentially in the openings are overlapping cuts.

2. The apparatus of claim 1 wherein the openings in the guide body are overlapping from the top surface to the bottom surface of the guide body.

3. A surgical instrument for shaping the distal femur of a patient to receive a unicondylar prosthetic component, comprising:
   a) a cutting guide body having a peripheral sidewall, a bottom surface for abutting the patient's distal femur during use, and a top surface for receiving a bone cutting reamer;
   b) means for affixing the guide body to the distal femur in a desired position;
   c) first and second cylindrically shaped openings in the guide body surrounded by the peripheral side wall of the guide body, said opening extending between the upper and lower surfaces of the guide body;
   d) each of the openings providing a central axis, and the respective axes of the openings forming an acute angle;
   e) a bone cutting reamer that registers in a selected opening of the guide body, wherein the opening positions the reamer for shaping the distal femur of a patient; and
   f) wherein the cutting guide body has an upper surface defined by a first surface that surrounds the first opening in the guide body and a second surface that surrounds the second opening in the cutting guide body.

4. The apparatus of claim 1 wherein the reamer has an annular member that engages the top of the guide body during use so that the combination of the annular member and the upper surface of the guide body defines the depth of cut of the reamer.

5. The apparatus of claim 1 wherein the reamer is a rotary reamer comprised of a shaft, an enlarged cylindrically shaped lower distal end portion, a collar that extends around the upper end portion of the cylindrically shaped portion, and the cylindrically shaped portion having a flat lowermost end surface with cutting blades extending therefrom.

6. The apparatus of claim 1 wherein there is further included an annular bushing that removably fits each of the cylindrically shaped openings, and the bushing has an internal bore that receives the reamer during use.

7. A surgical instrument for shaping the distal femur of a patient to receive a unicondylar prosthetic component, comprising:
  a) a cutting guide body having a peripheral sidewall, a bottom surface for abutting the patient's distal femur during use, and a top surface for receiving a bone cutting reamer;
  b) means for affixing the guide body to the distal femur in a desired position;
  c) a pair of cylindrically shaped openings in the guide body surrounded by the peripheral side wall of the guide body, and each opening extending between the upper and lower surfaces of the guide body
  d) each of the openings providing a central axis, and the respective axes of the openings forming an acute angle;
  e) an annular bushing that registers in a selected of the cylindrical openings, the bushing having a central cylindrical opening that receives a reamer during use;
  f) a bone cutting reamer that registers in the opening of the bushing when the bushing is in operative position in a selected guide body opening, wherein the combination of the bushing and guide block opening positions the reamer for shaping the distal femur of a patient; and
  g) wherein the reamer is positioned to cut overlapping convex surfaces on the patients distal femur when the reamer and bushing are sequentially placed in the angled, cylindrically shaped openings.

8. The apparatus of claim 7 wherein the reamer has an arcuate cutting edge and a portion of the openings is overlapping so that the cuts formed by the reamer when placed sequentially in the openings are overlapping cuts.

9. The apparatus of claim 8 wherein the openings in the guide body are overlapping from the top surface to the bottom surface of the guide body, and the bushing extends during use at least partially into each opening.

10. The apparatus of claim 7 wherein the cutting guide body has an upper surface defined by a first surface that surrounds a first opening in the guide body and a second surface that surrounds a second opening in the cutting guide body, and the bushing registers upon the upper surface of a selected opening during use.

11. The apparatus of claim 7 wherein the reamer has an annular member that engages the top of the bushing during use so that the combination of the annular member and the position of the bushing on the guide body defines the depth of cut of the reamer.

12. The apparatus of claim 7 wherein the reamer is a rotary reamer comprised of a shaft, an enlarged cylindrically shaped lower distal end portion, a collar that extends around the upper end portion of the cylindrically shaped portion, and the cylindrically shaped portion having a flat lowermost end surface with cutting blades extending therefrom.

13. The apparatus of claim 7 wherein the reamer has an arcuate cutting blade for forming convex circular cuts on the patient's distal femur.

* * * * *